United States Patent [19]

Beachley, Jr.

[11] Patent Number: 5,003,092

[45] Date of Patent: Mar. 26, 1991

[54] USE OF $R_2MR'$ TO PREPARE SEMICONDUCTOR AND CERAMIC PRECURSORS

[75] Inventor: Orville T. Beachley, Jr., Buffalo, N.Y.

[73] Assignee: The Research Foundation of State University of NY, Albany, N.Y.

[21] Appl. No.: 360,394

[22] Filed: Jun. 2, 1989

[51] Int. Cl.$^5$ ............................. C07F 5/00; C07F 5/06
[52] U.S. Cl. ........................................ 556/1; 556/170; 556/174; 556/176; 556/30; 556/14; 556/19
[58] Field of Search ................... 556/1, 14, 19, 30, 64, 556/170, 174, 176

[56] References Cited

U.S. PATENT DOCUMENTS 4,740,606  4/1988  Melas ...................................... 556/1
4,759,917  7/1988  Coleman et al. .................... 556/1 X

OTHER PUBLICATIONS

A. H. Cowley, B. L. Benac et al., "Organometallic Chemical Vapor Deposition of III/V Compound Semiconductors with Novel Organometallic Precursors," *J. Am. Chem. Soc.*, 110, 6248–6249, 1988.

*Primary Examiner*—Arthur C. Prescott
*Attorney, Agent, or Firm*—Michael L. Dunn; Ellen K. Park

[57] ABSTRACT

Cyclopentadienyl compounds of aluminum, gallium and indium which when reacted at low temperature with amines, phosphines and arsines form compounds which are potential precursors to ceramic materials and semiconductors.

19 Claims, No Drawings

USE OF R₂MR' TO PREPARE SEMICONDUCTOR AND CERAMIC PRECURSORS

This invention was made with Government support under Contract N00014-87-K-0266 awarded by the Department of the Navy. The Government may have certain rights in this invention.

BACKGROUND OF THE INVENTION

In the conventional preparation of semiconductors a predetermined amount of extremely pure metal phosphide or arsenide is laid down on a substrate crystal. The conventional method of carrying out this process is to charge predetermined amounts of phosphine or arsine into a stream of hydrogen together with the appropriate amount of an organometallic compound. The mixed gas stream is passed through a furnace, at a predetermined temperature, which contains the crystal on which deposition is desired. At the predetermined temperature, an elimination reaction takes place whereby the organic portion of the organometallic is eliminated and replaced by phosphorus or arsenic as is appropriate. In order for this reaction to take place properly and efficiently the organometallic utilized must be sufficiently stable under the furnace conditions that it does not decompose per se and yet it must be sufficiently reactive to permit the elimination reaction to occur substantially instantaneously when the gas stream enters the heated furnace area.

Heretofore, the organic group used in the synthesis of the organometallic compounds has been the methyl group. However, the metalomethyls of this group are extremely volatile and pyrophoric, i.e., should the organometallic accidentally come into contact with air due to process errors, it would spontaneously inflame. This handling disadvantage makes it desirable to utilize alternative compounds.

The ethyl, isopropyl and isobutyl derivatives decompose too readily at elevated temperatures to permit the elimination reaction to take place in the proper manner.

In addition, a significant disadvantage of preparing semiconductors from phosphine and arsine is that these compounds are toxic and are stored as high pressure gases.

It has also been disclosed that organometallic molecules having $\sigma$ bonding between the Group III and Group V elements are effective precursors for the preparation of III/V compound semiconductor materials (A. H. Cowley, B. L Benac et al., "Organometallic Chemical Vapor Deposition of III/V Compound Semiconductors with Novel Organometallic Precursors", J. Am. Chem. Soc., 110, 6248–6249, 1988). These precursors have been found to be stable toward air and moisture, and are also sufficiently volatile for use in the gas phase synthesis of semiconductor materials. However, these precursors are made via a metathesis reaction or at high temperatures. In addition, lithium, sodium and potassium derivatives of Group V compounds and halogen derivatives of Group III compounds are used to make the precursors which add impurities to the final product.

Therefore, there still exists a need for a cleaner method which can take place at lower temperatures to minimize the amount of impurities.

SUMMARY OF THE INVENTION

The invention comprises a method of preparing a compound having the formula $R_2MYR'_{2-n}H_n$, where R is an organic group, M is selected from the group consisting of Al, Ga and In, Y is selected from the group consisting of N, P and As, R' is an organic group and n is an integer independently selected from 0-2; which comprises reacting $R_2MR''$ with $R'_{3-m}YH_m$ where R, M, Y and R' are as defined above, m is an integer independently selected from 1-3 and R" is selected from the group consisting of cyclopentadienyl, allyl, alkynyl, and vinyl.

DETAILED DESCRIPTION OF THE INVENTION

In accordance with this invention, suitable organic groups are those which undergo the elimination reaction readily yet are resistant to self decomposition during volatilization. Such groups may, for example, be independently selected from substituted and unsubstituted alkyl, cycloalkyl, aryl, alkenyl, cycloalkenyl and alkynyl.

By the term alkyl, alkenyl and alkynyl is meant alkyl, alkenyl and alkynyl hydrocarbons having from about 1 to about 20 carbon atoms and preferably from about 1 to about 12 carbon atoms. Such hydrocarbons can be straight chained or branched and include isomers thereof. Thus, the term alkyl includes methyl, ethyl, n-propyl, i-propyl, n-butyl, t-butyl, i-butyl, pentyl, hexyl, heptyl and the like up to about 20 carbon atoms.

Similarly the terms alkenyl and alkynyl include unsaturated hydrocarbons having one or more double and triple bonds therein such as vinyl, propenyl, butenyl, ethynyl and the like up to about 20 carbon atoms and preferably from about 1 to about 12 carbon atoms.

By the terms cycloalkyl and cycloalkenyl is meant the alicyclic saturated and unsaturated hydrocarbons containing up to about 20 carbon atoms and preferably from about 1 to about 12 carbon atoms, such as cyclopropyl, methylcyclopropyl, cyclobutyl, ethylcyclobutyl, cyclopentyl, cyclohexyl, cyclobutadienyl, cyclohexadienyl and the like.

By the term aryl, is meant cyclic aromatic, such as phenyl and naphthyl, and heteroaromatic structures.

R" may be a cyclopentadienyl, allyl, alkynyl or vinyl substituent. It is understood that the terms cyclopentadienyl, allyl, alkynyl and vinyl include both substituted and unsubstituted groups. Examples of suitable reactants having the formula $R_2MR''$, and meeting the above definitions of R, M and R" include but are not limited to dimethyl(cyclopentyldienyl) metal compounds. An example of a dimethyl(cyclopentyldienyl) metal compound is dimethylgallium cyclopentadienide. These compounds are commercially available or may be synthesized by using procedures well known to those skilled in the art. For example, the reactant $Me_2Ga(C_5H_5)$ may be synthesized by reacting a sufficient amount of $Ga(C_5H_5)_3$ with $GaMe_3$ in pentane. The reaction mixture is warmed to ambient temperature and stirred for a sufficient time to allow the reaction to take place. The solvent is then removed by a suitable means and the product is sublimed.

Appropriate substituents meant to be included for substitution on the unsaturated hydrocarbon moieties include but are not limited to alkyl, cycloalkyl, aryl, alkenyl, cycloalkenyl, haloalkyl, amine, alkylamine, alkenylamine, cycloalkylamine, arylamine, aminoalkyl, aminoalkenyl, aminocycloalkyl, aminoaryl, and mixtures thereof.

The above reactant ($R_2MR''$) is reacted with an amine, phosphine or arsine, having the structure $R'_{3-m}YH_m$ where Y is N, P or As, m is an integer 1-3, to obtain the product in accordance with the invention. Examples of suitable amines, phosphines and arsines having the above structure are as follows: cyclohexylamine, N-methylcyclohexylamine, tert-butylamine, diethylamine, N-methylphenylamine, N-ethylphenylamine, ammonia, methylamine, methylphosphine, ethylphosphine, i-propylphosphine, t-butylphosphine, di(t-butyl)phosphine, dimethylphosphine, diethylphosphine, methylphenylphosphine, dicyclohexylphosphine, diphenylphosphine, methylarsine, ethylarsine, i-propylarsine, t-butylarsine, di(t-butyl)arsine, dimethylarsine, and diethylarsine.

The general reaction is as follows: A stoichiometric amount of the reactant $R_2MR''$ is mixed with a predetermined amount of solvent, i.e., an amount sufficient to form a solution of the product. The solvent is generally an organic solvent. By organic solvent is meant a non-aqueous liquid such as hydrocarbons but does not include solvents having acidic protons. Examples of suitable solvents include but are not limited to benzene or pentane. The desired reactant having the formula $R'_{3-m}YH_m$ is added at a low temperature to the solution and the solution is stirred until the reaction is complete. By low temperature is meant between about $-80°$ C. to about ambient temperature. By ambient temperature is meant a temperature between about 20° C. to about 27° C. It is preferred that the reaction take place at the lowest possible temperature to decrease the formation of impurities. The reaction mixture is then filtered. The filtrate is cooled to a temperature sufficient to induce crystallization. The solvent, cyclopentadiene and possibly excess starting material is removed by vacuum distillation or other suitable methods to leave the end product, i.e., $R_2MYR'_{2-n}H_n$. The end product is then purified by a suitable procedure such as vacuum sublimation or recrystallization, depending upon the nature of the product. For example, where the product is dimethylgallium tert-butylamide, sublimation can be utilized.

As an example, $Me_2Ga(C_5H_5)$ may be reacted with $R'_{3-m}YH_m$ (Y=N, P). In a typical reaction, dry, freshly purified amine or phosphine is vacuum distilled or syringed into a tared tube equipped with a Teflon valve and a 14/35 (standard taper) joint. Then, a stoichiometric amount of $Me_2Ga(C_5H_5)$ is placed into a two-neck flask equipped with a magnetic stirbar, a Teflon valve adapter and the tube containing the amine or phosphine. Benzene or pentane, 35 ml, is vacuum distilled onto the $Me_2Ga(C_5H_5)$ and the flask is warmed to ambient temperature. The desired amine or phosphine is added to the solution by opening the valve on the tube and the resulting colorless solution is stirred overnight. The reaction mixture is then filtered by using a medium glass frit. With the filtrate cooled to $-10°$ C., the solvent, cyclopentadiene and possibly excess starting material is removed by vacuum distillation to leave an off-white product. The product is then finally purified by vacuum sublimation or recrystallization depending upon the nature of the product, $Me_2GaYR'_{2-n}H_n$.

The compounds made in accordance with this invention were shown to be substantially purer than those disclosed in the literature (Stadelhofer, J., Weidlein, J., *Organomet. Chem.* 1975, 84, Cl.; Beachley, O. T., Jr.; Bueno, C.; Churchill, M. R.; Hallock, R. B.; Simmons, R. G., *Inorg. Chem.* 1981, 20, 2423; Coates, G. E., *J. Chem. Soc.*, 1951, 2003; Storr, A. J., *Chem. Soc.* (A) 1968, 2605; Coates, G. E., Graham, J. J., *Chem. Soc.*, 1963, 233).

The end product may then be used as a precursor for ceramic materials and semiconductors such as Group III/V ceramics and semiconductors.

The following examples and preparations describe the manner and process of making and using the invention and set forth the best mode contemplated by the inventor of carrying out the invention, but are not to be construed as limiting.

EXAMPLES

Example 1

The reactant $Me_2Ga(C_5H_5)$ may be synthesized as follows: A 2.24 g (8.45 mmol) sample of $Ga(C_5H_5)_3$ was placed into a two-neck reaction flask equipped with a magnetic stirbar and an adapter with a Teflon valve. Pentane, 50 ml, was vacuum distilled onto the $Ga(C_5H_5)_3$. Then, 1.94 g (16.9 mmol) of $GaMe_3$ was condensed into the reaction flask that was cooled to $-196°$ C. After the reaction mixture was warmed to ambient temperature and stirred for one hour, the solvent was removed by vacuum distillation. The original reaction flask was then connected to a clean 100 ml Schlenk flask by means of an elbow with 14/35 and 24/40 (standard taper) joints and evacuated. The product was sublimed at 60° C. into the clean flask, which was cooled to $-196°$ C. Dimethylgallium cyclopentadienide, $Me_2Ga(C_5H_5)$ (3.95 g, 24.0 mmol, 94.7% yield), was isolated as a colorless solid at ambient temperature.

The product was confirmed as $Me_2Ga(C_5H_5)$ by using various known and accepted indicia including NMR and IR analysis and found to have the following properties: mp 97.5-99° C.; $^1H$ NMR ($C_6D_6$, 1% $C_6H_6$) δ 6.20 ($C_5H_5$, 5H), $-0.41$ ($CH_3$, 6H); ($CCl_4$) 6.29 (s, $C_5H_5$, 5H), $-0.31$ (s, Me, 6H). IR (Nujol mull, cm$^{-1}$) 3100 (w), 3080 (w), 1776 (w), 1720 (w), 1620 (w), 1399 (m), 1360 (m), 1342 (m), 1192 (m), 1181 (m), 1068 (w), 1056 (w), 1002 (w), 984 (m), 879 (w), 872 (m), 854 (m), 836 (s), 813 (m), 797 (s), 745 (s), 717 (s), 602 (m), 578 (vs), 522 (m), 290(w). Anal. Calcd: C, 50.99: H, 6.72. Found: C, 50.82: H, 6.76.

Example 2

Synthesis of $[Me_2GaN(H)(C_6H_{11})]_2$: The preparation of $[Me_2GaN(H)(C_6H_{11})]_2$ used 0.207 g (2.09 mmol) of $H_2N(C_6H_{11})$, 0.344 g (2.09 mmol) of $Me_2Ga(C_5H_5)$ and pentane as the solvent. The product was purified by vacuum sublimation at 50°-60° C. to yield 0.259 g of dimethylgallium cyclohexylamide (1.31 mmol, 62.6% yield) as a colorless crystalline solid at ambient temperature.

The product was confirmed as dimethylgallium cyclohexylamide ($[Me_2GaN(H)(C_6H_{11})]_2$) by using various known and accepted indicia, including NMR and IR analysis and found to have the following properties: mp 98°-99.5° C. $^1H$ NMR ($C_6D_6$ 1%$C_6H_6$) δ 2.45 (m, H—N, 1H), 1.08 (m, $C_6H_{11}$, 11.7H), $-0.15$ (m, Ga—Me, 5.8). IR (Nujol mull, cm$^{-1}$) 3290 (w), 2960 (sh), 1465 (sh), 1445 (sh), 1435 (m), 1360 (m), 1345 (w), 1285 (w), 1260 (w), 1200 (m), 1190 (m), 1120 (w), 1060 (m), 1030 (w), 970 (m), 915 (w), 890 (m), 863 (m), 859 (m), 840 (m), 785 (w), 680 (w), 600 (m), 570 (m), 555 (m), 525 (m), 500 (w), 425 (w), 390 (w). Anal. Calcd: C, 48.54; H, 9.17. Found: C, 48.57; H, 9.09. Cryoscopic molecular weight, benzene solution, formula weight 198 (obsd molality, obsd mol wt, association): 0.0834, 432, 2.18; 0.0577, 447, 2.25; 0.0439, 465, 2.35.

Example 3

Synthesis of $[Me_2GaN(CH_3)(C_6H_{11})]_2$: The preparation of $[Me_2GaN(CH_3)(C_6H_{11})]_2$ used 0.300 g (2.65 mmol) of $HN(Me)(C_6H_{11})$, 0.439 g (2.65 mmol) of $Me_2Ga(C_5H_5)$ and pentane as the solvent. The product was sublimed at 80°–90° C. under dynamic vacuum to yield 0.500 g of dimethylgallium N-methyl,N-cyclohexylamide (2.36 mmol, 89.0% yield) as a colorless crystalline solid at ambient temperature.

The product was confirmed as $[Me_2GaN(CH_3)(C_6H_{11})]_2$ by using various known and accepted indicia including NMR and IR analysis and found to have the following properties: mp 158°–159° C. $^1H$ NMR $(C_6D_6)$ δ [2.228 (s, N—$CH_3$, cis), 2.176 (s, N—$CH_3$, trans), 3.0H], 1.204 (m, N—$C_6H_{11}$, [−0.100 (s, Ga—$CH_3$, cis), −0.180 (s, Ga—$CH_3$, cis) −0.135 (s, Ga—$CH_3$, trans), 5.8H]. IR (Nujol mull, $cm^{-1}$) 1490 (w), 1360 (s), 1345 (m), 1325 (w), 1300 (w), 1255 (m), 1248 (w), 1200 (vs), 1180 (W), 1140 (m), 1085 (m), 1050 (w), 1025 (w), 988 (w), 918 (vs), 890 (m), 875 (m), 840 (m), 780 (m), 735 (sh), 675 (m), 632 (m), 565 (vs), 528 (m), 435 (w), 390 (vw), 310 (w), 295 (vw), 285 (vw), 260 (w), 238 (m), 230 (w). Anal. Calcd: C, 50.99; H, 9.51. Found: C, 51.08; H, 9.68. Cryoscopic molecular weight, benzene solution, formula weight 212 (obsd molality, obsd mol wt, association): 0.0675, 441, 2.08; 0.0525, 426, 2.01; 0.0462, 422, 1.99.

Example 4

Synthesis of $[Me_2GaN(H)C(CH_3)_3]_2$: The preparation of $[Me_2GaN(H)C(CH_3)_3]_2$ used 0.151 g (2.06 mmol) of $H_2N[C(CH_3)_3]$, 0.340 g (2.06 mmol) of $Me_2Ga(C_5H_5)$ and pentane as the solvent. The product was sublimed at 40°–45° C. under dynamic vacuum to yield, 0.240 g of dimethylgallium tert-butylamide (1.40 mmol, 68.0% yield) as a colorless crystalline solid at ambient temperature.

The product was confirmed as $[Me_2GaN(H)C(CH_3)_3]_2$, by using various known and accepted indicia including NMR and IR analysis and found to have the following properties: mp 73.5°–75° C. $^1H$ NMR $(C_6D_6)$ δ 0.98 (s, C—$CH_3$, 9H), −0.06 (s, Ga—$CH_3$, 6H). IR (Nujol mull, $cm^{-1}$) 3250 (m), 1390 (w), 1360 (s), 1355 (m), 1230 (m), 1200 (s), 1187 (s), 1180 (m), 1030 (w), 1020 (w), 935 (s), 910 (s), 892 (s), 875 (m), 750 (s), 682 (m), 590 (s), 565 (s), 530 (s), 468 (w), 390 (w), 380 (sh). Anal. Calcd: C, 41.92; H, 9.38. Found: C, 42.06; H, 9 41. Cryoscopic molecular weight, benzene solution, formula weight 172 (obsd molality, obsd mol wt, association): 0.0660, 369, 2.14; 0.0496, 377, 2.19; 0.0306, 405, 2.36.

Example 5

Synthesis of $[Me_2GaN(C_2H_5)_2]_2$: The preparation of $[Me_2Ga(C_2H_5)_2]_2$ used 0.158 g (2.15 mmol) of $HN(C_2H_5)_2$, 0.355 g (2.15 mmol) of $Me_2Ga(C_5H_5)$ and benzene as the solvent. The product was sublimed at room temperature under vacuum to yield 0.296 g of dimethylgallium diethylamide (1.73 mmol, 80.5% yield) as a colorless crystalline solid at ambient temperature.

The product $[Me_2GaN(C_2H_5)_2]_2$, was confirmed by using various known and accepted indicia including NMR and IR analysis and found to have the following properties: mp 39°–40.5° C. $^1H$ NMR $(C_6D_6)$ δ 2.66 (q, $CH_2$, 2H, $^3J_{C-C-H}$7.12Hz), 0.73 (t, $CH_3$, 3.2, $^3J_{C-C-H}$7.2Hz), −0.20 (s, Ga—$CH_3$, 3.1H). IR (Nujol mull, $cm^{-1}$) 2720 (w), 1470 (sh), 1465 (sh), 1435 (sh), 1360 (sh), 1285 (w), 1200 (m), 1170 (w), 1140 (m), 1110 (w), 1040 (w), 1000 (m), 850 (w), 790 (m), 735 (sh), 670 (w), 590 (m), 560 (m), 530 (m). Anal. Calcd: C, 41.92; H, 9.38. Found: C, 42.18; H, 9.55. Cryoscopic molecular weight, benzene solution, formula weight 172 (obsd molality, obsd mol wt, association): 0.0733, 382, 2.22; 0.0582, 387, 2.25; 0.0369, 410, 2.38.

Example 6

Synthesis of $[Me_2GaN(CH_3)(C_6H_5)]_2$: The preparation of $[Me_2GaN(CH_3)(C_6H_5)]_2$ used 0.322 g (3.01 mmol) of $HN(CH_3)(C_6H_5)$, 0.499 g (3.02 mmol) of $Me_2Ga(C_5H_5)$ and benzene as the solvent. The product was sublimed at 120° C. under dynamic vacuum to yield 0.476 g of dimethylgallium N-methylanilide (2.31 mmol, 76.5% yield) as a colorless crystalline solid.

The product $[Me_2GaN(CH_3)(C_6H_5)]_2$ was confirmed by using various known and accepted indicia including NMR and IR analysis and found to have the following properties: mp 109°–111° C.; $^1H$ NMR $(C_6D_6)$ δ 2.82 (s, N—Me, cis), 2.74 (s, N—Me, trans), 0.11 (s, Ga—Me, cis), −0.10 (s, Ga—Me, trans), −0.18 (s, Ga—Me, cis). $^{13}C\{^1H\}$ NMR $(C_6D_6)$ δ 49.39 (s, N—Me, cis), 45.38 (s, N—Me, trans), −2.45 (s, Ga—Me, trans), −3.42 (s, Ga—Me, cis), −6.95 (s, Ga—Me, cis). IR (Nujol mull, $cm^{-1}$) 1590 (s), 1575 (m), 1547 (w), 1490 (vs), 1459 (s), 1380 (m), 1295 (w), 1204 (m), 1197 (s) 1162 (m), 1151 (m), 1082 (w), 1041 (w), 1019 (m), 1000 (w), 896 (w), 788 (s), 765 (s), 730 (s), 701 (s), 588 (m), 562 (s), 533 (s), 440 (s).

Example 7

Synthesis of $[Me_2GaN(C_2H_5)(C_6H_5)]_2$: The preparation of $[Me_2GaN(C_2H_5)(C_6H_5)]_2$ used 0.361 g (2.98 mmol) of $HN(C_2H_5)(C_6H_5)$, 0.494 g (2.99 mmol) of $Me_2Ga(C_5H_5)$ and pentane as the solvent. The product was sublimed at 110° C. under dynamic vacuum to yield 0.574 g of dimethylgallium N-ethylanilide (2.61 mmol, 87.3% yield) as a colorless crystalline solid at ambient temperature.

The product $[Me_2GaN(C_2H_5)(C_6H_5)]_2$, was confirmed by using various known and accepted indicia including NMR and IR analysis and found to have the following properties: mp 97°–98° C. $^1H$ NMR $(C_6D_6)$ δ 3.23 (q, N—$CH_3$, cis), 3.19 (q, N—$CH_2$, trans), 0.76 (t, —Me, cis), 0.68 (t, —Me, trans), 0.16 (s, Ga—Me, cis), −0.03 (s, Ga—Me, trans), −0.27 (s, Ga—Me, cis). $^{13}C\{^1H\}$ NMR $(C_6D_6)$ δ 51.56 (s, N—$CH_2$, cis), 49.77 (s, N—$CH_2$, trans), 14.23 (s, —Me, cis), 14.07 (s, —Me, trans), −3.70 (s, Ga—Me, trans), −4.13 (s, Ga—Me, cis), −6.24 (s, Ga—Me, cis). IR (Nujol mull, $cm^1$) 1735 (vw), 1595 (m), 1581 (sh, m), 1488 (s), 1259 (w), 1204 (m), 1192 (m), 1152 (w), 1135 (w), 1085 (m), 1075 (sh, w), 1022 (m), 920 (vw), 913 (m), 890 (w), 838 (w), 772 (m), 760 (m), 731 (m), 697 (s), 633 (w), 585 (w), 570 (w), 529 (m). Anal. Calcd: C, 54.60; H, 7.33. Found: C, 54.41; H, 7.49. Cryoscopic molecular weight, benzene solution, formula weight 220 (obsd molality, obsd mol wt, association): 0.0821, 482, 2.19; 0.0474, 489, 2.22; 0.0259, 492, 2.24.

Example 8

Synthesis of [Me$_2$GaNH$_2$]$_3$: The preparation of [Me$_2$GaNH$_2$]$_3$ used 0.0851 g (5.00 mmol) of NH$_3$, 0.824 g (5.00 mmol) of Me$_2$Ga(C$_5$H$_5$) and pentane as the solvent. The product was sublimed at 90° C. under dynamic vacuum to yield 0.540 g of dimethylgallium amide (4.67 mmol, 93.4% yield) as a colorless crystalline solid at ambient temperature.

The product [Me$_2$GaNH$_2$]$_3$, was confirmed by using various known and accepted indicia including NMR and IR analysis and found to have the following properties: mp 100°–101.5° C.; $^1$H NMR (C$_6$D$_6$) δ 0.41 (CH$_3$). IR (Nujol mull, cm$^{-1}$) 3520 (w), 3440 (w), 1640 (m), 1600 (w), 1475 (sh), 1430 (vs), 1395 (m), 1360 (s), 1285 (w), 1265 (w), 1235 (s), 1200 (w), 1190 (w), 1120 (w), 1080 (w), 1015 (w), 930 (w), 915 (w), 880 (m), 820 (w), 800 (w), 770 (w), 640 (w), 620 (w), 510 (w), 460 (w), 380 (w), 340 (w). Anal. Calcd: C, 20.74; H, 6.96. Found: C, 21.04; H, 6.99. Mass Spectrum, EI, m/e, formula mass 345 (rel. intensity, identity): 346 (0.91, M$_3$+), 332 (73.12, M$_3$—CH$_3$+), 217 (100, M$_2$—CH$_3$+), 99 (59.90, M$_1$—NH$_2$+).

Example 9

Synthesis of [Me$_2$GaN(H)(CH$_3$)]$_3$: The preparation of [Me$_2$GaN(H)(CH$_3$)]$_3$ used 1.53 mmol of H$_2$NCH$_3$, 0.252 g (1.53 mmol]) of Me$_2$Ga(C$_5$H$_5$) and pentane as the solvent. The product was sublimed twice at ambient temperature to yield 0.177 g of dimethylgallium methylamide (1.37 mmol, 89.5% yield) as a colorless crystalline solid at ambient temperature.

The product [Me$_2$GaN(H)(CH$_3$)]$_3$, was confirmed by using various known and accepted indicia including NMR and IR analysis and found to have the following properties: mp 117°–119° C. $^1$H NMR (C$_6$D$_6$) δ 1.95 (m, N—CH$_3$, 3.0H), −0.348(m, Ga—CH$_3$, 5.8H). IR (Nujol mull, cm$^{-1}$) 3270 (w), 1515 (sh), 1505 (s), 1472 (m), 1462 (w), 1430 (w, br), 1200 (m), 1195 (m), 1138 (w), 1040 (m), 985 (m), 970 (m), 942 (m), 925 (m), 680 (m, br), 565 (s), 542 (s), 522 (vs), 431 (w), 275 (w). Mass Spectrum, EI, m/e, formula mass 387 (rel. intensity, identity): 374 (62.41, M$_3$—CH+), 245 (100.00, M$_2$—CH+), 214 (21.64, M$_2$—N(CH$_3$)$_2$+), 99 (22.66, Ga(CH$_3$)$_2$+).

Example 10

Synthesis of [Me$_2$GaP(CH$_3$)(C$_6$H$_5$)]$_3$: The preparation of [Me$_2$GaP(CH$_3$)(C$_6$H$_5$)]$_3$: The preparation of [Me$_2$GaP(CH$_3$)(C$_6$H$_5$)]$_3$ used 0.361 g (2.91 mmol) of HP(CH$_3$)(C$_6$H$_5$), 0.481 g (2.91 mmol) of Me$_2$Ga(C$_5$H$_5$) and benzene as the solvent. The product was recrystallized from pentane solution at −40° C. to yield 0.435 g of dimethylgallium methylphenylphosphide (1.95 mmol, 67.0% yield) as a colorless crystalline solid at ambient temperature.

The product [Me$_2$GaP(CH$_3$)(C$_6$H$_5$)]$_3$, was confirmed by using various known and accepted indicia including NMR and IR analysis and found to have the following properties:mp 124°–126° C. $^1$H NMR (C$_6$D$_6$) δ 1.39 (m, P—Me, 3H), −0.08 (m Ga—Me, 6H) $^{13}$C{$^1$H} NMR (C$_6$D$_6$) δ 4.22 (m, P—Me), −9.28 (m, Ga—Me). $^{31}$P{$^1$H} NMR (C$_6$D$_6$) δ78.79, 77.70 (relative intensities are 1.00 and 2.05 respectively). IR (Nujol mull, cm$^{-1}$) 1193 (w), 1183 (w), 1165 (vw), 1022 (w), 998 (w), 855 (sh, m), 880 (m), 737 (s), 719 (s), 690 (w), 555 (m), 521 (m), 480 (w). Anal. Calcd: C, 48.64; H, 6.48; P, 13.76. Found: C, 48.49; H, 6.33; P, 13.90. Cryoscopic molecular weight, benzene solution, formula weight 223 (obsd molality, obsd mol wt, association): 0.0506, 772, 3.46; 0.0372, 733, 3.29; 0.0177, 741, 3.32.

Example 11

Synthesis of [Me$_2$GaP(C$_6$H$_{11}$)$_2$]$_2$: The preparation of [Me$_2$Gap(C$_6$H$_{11}$)$_2$]$_2$ used 0.506 g (2.55 mmol) of HP(C$_6$H$_{11}$)$_2$, 0.420 g (2.55 mmol) of Me$_2$Ga(C$_5$H$_5$) and pentane as the solvent. The product was recrystallized from pentane at −35° C, to yield 0.6130 g of dimethylgallium dicyclohexylphosphide (2.06 mmol, 80.8% yield) as a colorless crystalline solid at ambient temperature.

The product [Me$_2$GaP(C$_6$H$_{11}$)$_2$]$_2$, was confirmed by using various known and accepted indicia including NMR and IR analysis and found to have the following properties:mp 161°–163° C. $^1$H NMR (C$_6$D$_6$) δ 1.35 (m, C$_6$H$_{11}$, 22.6H), 0.10 (t, CH$_3$, 6.0H, $^3$J$_{P-Ga-C}$4.5Hz). IR (Nujol mull, cm$^{-1}$) 1360 (m), 1348 (vw), 1336 (w), 1290 (vw), 1285 (vw), 1260 (w), 1182 (m), 1168 (m), 1111 (w), 1080 (vw), 1065 (vw), 1040 (vw), 1020 (vw), 995 (m), 908 (vw), 890 (w), 880 (m), 845 (m), 740 (m), 665 (w), 550 (m), 520 (m), 460 (vw), 308 (w). Anal. Calcd: C, 56.6: H, 9.50. Found: C, 56.35; H. 9.50. Mass Spectrum, EI, m/e formula mass 594 (rel. intensity, identity): 579 (27.30, M$_2$—CH$_3$+), 397 (100.0 M$_2$—P(C$_6$H$_{11}$)$_2$+), 281 (42.03, M$_1$—CH$_3$+).

Example 12

Synthesis of (Me$_2$GaPPh$_2$)$_2$: The preparation of (Me$_2$GaPPh$_2$)$_2$ used 0.398 g (2.14 mmol) of HPPh$_2$, 0.356 g (2.14 mmol) of Me$_2$Ga(C$_5$H$_5$) and pentane as the solvent. Within five minutes of the reagents being mixed at ambient temperature, an insoluble colorless crystalline product formed. The resulting crystalline product was washed five times with pentane and then was recrystallized from benzene to yield 0.537 g of dimethylgallium diphenylphosphide (1.89 mmol, 88.3% yield) as a colorless crystalline solid at room temperature.

The product (Me$_2$GaPPh$_2$)$_2$, was confirmed by using various known and accepted indicia including NMR and IR analysis and found to have the following properties:mp 214°–217° C.; $^1$H NMR (C$_6$D$_6$) δ 0.313, 0.303, 0.293, 0.283 (m, Ga—CH$_3$). $^{31}$P (C$_6$D$_6$) δ −45.9. IR (Nujol mull cm$^{-1}$) 3100 (w), 3070 (w), 3050 (w), 2720 (w), 2670 (w), 1580 (w), 1565 (vw), 1475 (vs), 1362 (vs), 1300 (m), 1258 (w), 1200 (w), 1185 (m), 1165 (w), 1155 (m), 1085 (W), 1065 (w), 1030 (w), 1020 (w), 998 (m), 970 (m), 915 (w), 885 (w), 840 (w), 745 (sh), 735 (vs), 690 (s), 670 (m), 555 (m), 520 (m), 503 (m), 475 (w), 435 (w), 390 (w). Anal. Calcd: C 59.01; H, 5.66. Found: C, 58.73; H, 6.05. Mass Spectrum, EI, m/e, formula mass 568 (rel. intensity, identity): 370 (86.87, M$_2$—(CH$_3$)$_3$(C$_6$H$_5$)+), 183 (100, (CH$_3$)$_3$Ga$_2$+), 108 (65.19 P(C$_6$H$_5$)+).

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A method of preparing a compound having the formula R$_2$MYR'$_{2-n}$H$_n$, where R is an organic group, M is selected from the group consisting of Al, Ga and In, Y is selected from the group consisting of N, P and As, R' is an organic group and n is an integer selected from 0–2; which comprises reacting R$_2$MR'' with $R'_{3-m}YH_m$ where R, M, Y and R' are as defined above, m is an integer selected from 1-3 and R" is selected from the group consisting of cyclopentadienyl, allyl, alkynyl and vinyl.

2. The method as recited in claim 1 wherein R and R' are independently selected from substituted and unsubstituted alkyl, cycloalkyl, aryl, alkenyl, cycloalkenyl and alkynyl.

3. The method as recited in claim 2 wherein R" is a cyclopentadienyl group.

4. The method as recited in claim 3 wherein R" is an unsubstituted cyclopentadienyl group.

5. The method as recited in claim 3 wherein R" is a substituted cyclopentadienyl group.

6. The method as recited in claim 4 wherein $R_2MR''$ is dimethylgallium cyclopentadienide.

7. The method as recited in claim 4 wherein $R_2MR''$ is diethylgallium cyclopentadienide.

8. The method as recited in claim 5 wherein $R_2MR''$ is dimethylgallium methylcyclopentadienide.

9. The method as recited in claim 3 wherein the organic groups are independently selected from the group consisting of methyl, ethyl, n-propyl, i-propyl, n-butyl, t-butyl, i-butyl, pentyl, hexyl and heptyl.

10. The method as recited in claim 3 wherein the reaction occurs at low temperatures between about $-80°$ C. to ambient temperature.

11. The method as recited in claim 3 wherein $R_2MR''$ is dimethylgallium cyclopentadienide, $R'_{3-m}YH_m$ is cyclohexylamine and $R_2MYR'_{2-n}H_n$ is dimethylgallium cyclohexylamide.

12. The method as recited in claim 3 wherein $R_2MR''$ is dimethylgallium cyclopentadienide, $R'_{3-m}YH_m$ is N-methylcyclohexylamine and $R_2MYR'_{2-n}H_n$ is dimethylgallium N-methyl, N-cyclohexylamide.

13. The method as recited in claim 3 wherein $R_2MR''$ is dimethylgallium cyclopentadienide, $R'_{3-m}YH_m$ is tert-butylamine and $R_2MYR'_2H_n$ is dimethylgallium tert-butylamide.

14. The method as recited in claim 3 wherein $R_2MR''$ is dimethylgallium cyclopentadienide, $R'_{3-m}YH_m$ is diethylamine and $R_2MYR'_{2<n}H_n$ is dimethylgallium diethylamide.

15. The method as recited in claim 3 wherein $R_2MR''$ is dimethylgallium cyclopentadienide, $R'_{3-m}YH_m$ is methylphenylphosphine and $R_2MYR'_{2-n}H_n$ is dimethylgallium methylphenylphosphide.

16. The method as recited in claim 3 wherein $R_2MR''$ is dimethylgallium cyclopentadienide, $R'_{3-m}YH_m$ is N-ethylphenylamine and $R_2MYR'_{2-n}H_n$ is dimethylgallium N-ethylanilide.

17. The method as recited in claim 3 wherein $R_2MR''$ is dimethylgallium cyclopentadienide, $R'_{3-m}YH_m$ is methylphenylphosphine and $R_2MYR'_{2-n}H_n$ is dimethylgallium methylphenylphosphide.

18. The method as recited in claim 3 wherein $R_2MR''$ is dimethylgallium cyclopentadienide, $R'_{3-m}YH_m$ is dicyclohexylphosphine and $R_2MYR'_{2-n}H_n$ is dimethylgallium dicyclohexylphosphide.

19. The method as recited in claim 3 wherein the compound $R'_2MYR_{2-n}H_n$, is a precursor for ceramic materials and semiconductors.

* * * * *

UNITED STATES PATENT AND TRADEMARK OFFICE
CERTIFICATE OF CORRECTION

PATENT NO. : 5,003,092

DATED : March 26, 1991

INVENTOR(S) : Orville T. Beachley, Jr.

It is certified that error appears in the above-identified patent and that said Letters Patent is hereby corrected as shown below:

Column 10, line 7: delete "$R_2MYR'_2H_n$", insert --$R_2MYR'_{2-n}H_n$--

Column 10, line 11: delete "$R_2MYR'2<_nH_n$", insert --$R_2MYR'_{2-n}H_n$--

Column 10, line 15: delete "methylphenylphosphine", insert --N-methylphenylamine--

Column 10, line 16: delete "methylphenylphosphide", insert --N-methylanilide--.

Signed and Sealed this

Twentieth Day of October, 1992

Attest:

DOUGLAS B. COMER

Attesting Officer     Acting Commissioner of Patents and Trademarks

UNITED STATES PATENT AND TRADEMARK OFFICE
CERTIFICATE OF CORRECTION

PATENT NO. : 5,003,092
DATED : Mar. 26, 1991
INVENTOR(S) : Orville T. Beachley, Jr.

It is certified that error appears in the above—identified patent and that said Letters Patent is hereby corrected as shown below:

In column 4, line 40, delete "$(C_5H_{5,5}H)$" and insert -- $(C_5H_5, 5H)$ --. In column 7, line 13, delete "0.41 $(CH_3)$" and insert -- -0.41 $(CH_3)$ --.

Signed and Sealed this

Twentieth Day of July, 1993

Attest:

MICHAEL K. KIRK

Attesting Officer       Acting Commissioner of Patents and Trademarks